(12) United States Patent
Bokel et al.

(10) Patent No.: US 7,528,256 B2
(45) Date of Patent: May 5, 2009

(54) PROCESS FOR THE PREPARATION OF NICOTINALDEHYDES

(75) Inventors: Heinz-Hermann Bokel, Darmstadt (DE); Mike Brandner, Büttelborn (DE); Ludwig Gantzert, Pfungstadt (DE); Ralf Knierieme, Groβ-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 569 days.

(21) Appl. No.: 10/554,061

(22) PCT Filed: Mar. 27, 2004

(86) PCT No.: PCT/EP2004/003272

§ 371 (c)(1),
(2), (4) Date: Oct. 24, 2005

(87) PCT Pub. No.: WO2004/094383

PCT Pub. Date: Nov. 4, 2004

(65) Prior Publication Data

US 2006/0199965 A1 Sep. 7, 2006

(30) Foreign Application Priority Data

Apr. 24, 2003 (DE) .............................. 103 18 690

(51) Int. Cl.
*C07D 213/46* (2006.01)

(52) U.S. Cl. ....................................... 546/315; 544/124
(58) Field of Classification Search ...................... None
See application file for complete search history.

(56) References Cited

U.S. PATENT DOCUMENTS 5,360,806 A 11/1994 Toki et al.

FOREIGN PATENT DOCUMENTS

EP 0 580 374 A 1/1994

OTHER PUBLICATIONS

Douat, Celine et al: "Synthesis of N—Protected .Alpha.-Amino Aldehydes From Their Morpholine Amide Derivatives" Tetrahedron Letters, 41(1), 37-40 Coden: TELAY; ISSN: 0040-4039, 2000, XP002286861; Seite 39-Seite 40; Tabel 1.
Sammakia, Tarek et al: "Enhanced Selectivities for the Hydroxyl-Directed Methanolysis of Esters Using the 2-Acyl-4-Aminopyridine Class of Acyl Transfer Catalysts: Ketones as Binding Sites" Journal of Organic Chemistry, 65(4), 974-978 Coden: JOCEAH; ISSN: 0022-3263, 2000, XP002286860.

*Primary Examiner*—Zinna N Davis
(74) *Attorney, Agent, or Firm*—Millen, White, Zelano, Branigan, P.C.

(57) ABSTRACT

The invention relates to a process for the preparation of nicotinaldehydes by reduction of the corresponding nicotinic acid morpholinamides.

20 Claims, No Drawings

PROCESS FOR THE PREPARATION OF NICOTINALDEHYDES

This application is a 371 of PCT/EP04/03272 filed Mar. 27, 2004.

The invention relates to a process for the preparation of nicotinaldehydes by reduction of the corresponding nicotinic acid morpholinamides.

Nicotinaldehydes are important intermediates or end products in industrial organic chemistry. Appropriately substituted derivatives, such as, for example, arylnicotinaldehydes, are, inter alia, valuable intermediates for the synthesis of highly value-added end products or are themselves such end products, in particular for crop protection, such as, for example, fungicides, insecticides, herbicides or pesticides, or for the preparation of highly pharmaceutically active substances.

There are preparation methods known from the literature which describe selective reduction of carboxylic acid derivatives as far as the aldehyde stage. These methods generally require cooling of the reaction mixture in order to minimise over-reductions.

Special methods for the reduction of nicotinic acid derivatives are also known. Thus, for example, DE-A 100 05 150 describes a process for the preparation of 5-arylnicotinaldehydes by reduction of the corresponding 5-arylnicotinic acids by means of catalytic hydrogenation. H. C. Brown and A. Tsukamoto in J. Am. Chem. Soc. 81, p. 502 (1959) described the reduction of nicotinamides using triethoxylithium aluminium hydride. However, a low reaction temperature was described as indispensable here, and the yield was below 90% of theory.

Further known processes for the preparation of nicotinaldehydes by reduction are shown in the following review.

| No. | Number of reaction steps | Nicotinic acid derivative | Reducing agent | Reaction conditions | Yield | Literature |
|---|---|---|---|---|---|---|
| 1 | 2 | diethylamide | $Cp_2Zr(H)Cl$ | room temp./ 15 min. | 99% | J. Am. Chem. Soc. 48 (2000) 11995-11996 |
| 2 | 3 | nitrile | DiBAH (di-isobutyl-aluminium hydride) | toluene −50° C. 2.5 hrs | 96% | J. Org. Chem. 64, 26 (1999) 9658-9667 |
| 3 | 3 | nitrile | K amyl-(9)-borabicyclo-nonane | THF 25° C. | 96% | Tetrahedron Letters 30, 28 (1989) 3677-3680 |
| 4 | 3 | nitrile | DiBAH | toluene −12° C. | 70% | J. Med. Chem. 36, 8 (1993) 953-966 |
| 5 | 2 | hydrazide | $NaIO_4$ | water/$NH_3$ | 70% | J. Am. Chem. Soc. 74 (1952) 5796 |
| 6 | 3 | N-methylanilide | $LiAlH_4$ | THF 0° C. | 65% | Angew. Chemie 65 (1953) 525 |
| 7 | 3 | nitrile | DiBAH | THF 0° C. | 62% | J. Med. Chem. 35, 21 (1992) 3784-3791 |
| 8 | 3 | sulfonylhydrazide | $Na_2CO_3$ | 160° C. ethylene glycol | 61% | J. Am. Chem. Soc. 80 (1958) 862 |
| 9 | 3 | nitrile | DiBAH | THF | 61% | J. Med. Chem. 34, 9 (1991) 2922-2925 |
| 10 | 2 | primary amide | $LiAlH(NEt_2)_3$ | room temp. 12 hrs | 53% | THL 32, 41 (1991) 6903-6904 |
| 11 | 2 | N-methoxy-N-methylamide | DiBAH | THF −100° C. | 51% | Heterocycles 53 (2000) 2183-2190 |

There is therefore interest in an extremely economical process for the production of these compounds on a large industrial scale.

As an unstable oxidation state between alcohol and carboxylic acid, aldehydes are generally accessible with difficulty. Aromatic aldehydes in particular easily oxidise to the corresponding carboxylic acids or disproportionate under alkaline conditions to give alcohol and carboxylic acid. In the reductive preparation of nicotinaldehyde derivatives, reduction to the dihydropyridine occurs as an additional side reaction.

It can be seen from the review that the known methods either require expensive reagents (Example Nos. 1, 3, 10), use raw materials which are not available in industrial quantities (Example Nos. 1, 3, 11), can only be carried out with the nitrile, which is itself prepared in three steps (Example Nos. 2, 3, 4, 7, 9) or require low temperatures (Example Nos. 2, 4, 11). From the point of view of the yield, only Example Nos. 1, 2 and 3 are economically viable. If the reagent costs are taken into account, only the process of Example No. 2 remains. However, the latter requires three reaction steps starting from nicotinic acid and relies on the maintenance of low temperatures.

Surprisingly, the inventors of the present patent application have now found that nicotinaldehydes can be obtained in virtually quantitative yields by reduction under standard conditions (room temperature, atmospheric pressure) if the starting materials employed are the corresponding morpholinamides.

Morpholinamides of nicotinic acid and derivatives thereof were previously unknown as aldehyde precursors.

The present invention thus relates to a process for the preparation of nicotinaldehydes, characterised in that the starting materials employed for the reduction are the corresponding morpholinamides. The said process is preferably carried out at room temperature and without pressure (under atmospheric pressure).

Reducing agents which are preferred in accordance with the invention here are lithium alkoxyaluminium hydrides containing one to three alkoxy radicals. The general formula is $LiAlH_{(4-n)}(OR)_n$, where n can be=1, 2 or 3. Suitable radicals are straight-chain or branched aliphatics, such as, for example, methyl, ethyl and tert-butyl. The reduction succeeds particularly selectively with $LiAlH(OEt)_3$. Likewise suitable as reducing agent for the preparation process according to the invention is the considerably cheaper $LiAlH_3(OEt)$.

In a preferred embodiment, nicotinic acid morpholinamides of the formula I

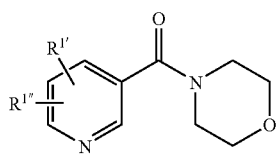

I in which $R^{1\prime}$, $R^{1\prime\prime\prime}$ each, independently of one another, denotes H, Hal, A, OA, $CH_2R^2$ or Ar, $R^2$ denotes OA or $NA_2$, A denotes unbranched or branched alkyl having 1-10 C atoms, in which one or two $CH_2$ groups may be replaced by O or S atoms and/or by —CH=CH— groups and/or also 1-7H atoms may be replaced by F, Ar denotes an unsaturated, partially or fully saturated, mono- or polycyclic homo- or heterocyclic system with the hetero atoms O, N, S which is unsubstituted or mono- or polysubstituted by Hal, A, OA, $NA_2$, $NO_2$, $NASO_2A$, $SO_2NA$, $SO_2A$, and Hal denotes F, Cl, Br or I, as starting materials are reduced to nicotinaldehydes of the formula II

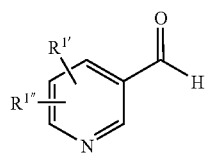

II

The above-mentioned radicals preferably have the following meanings here:

$R^{1\prime}$, $R^{1\prime\prime\prime}$ each, independently of one another, denotes H, Hal, A, OA, $CH_2R^2$ or Ar, where A, Ar, Hal and $R^2$ have one of the meanings described below. $R^{1\prime}$, $R^{1\prime\prime\prime}$ are, in particular, hydrogen, methoxy, ethoxy, propoxy, butoxy, fluorine, chlorine, bromine, iodine, phenyl or o, m or p-substituted phenyl. $R^{1\prime}$ is particularly preferably p-fluorophenyl or bromine and $R^{1\prime\prime\prime}$ is simultaneously hydrogen.

Hal denotes fluorine, chlorine, bromine or iodine, preferably fluorine, chlorine or bromine.

$R^2$ denotes OA or $NA_2$, where A has the meaning indicated above and below.

A denotes alkyl, is unbranched (linear) or branched, and has 1, 2, 3, 4, 5, 6, 7, 8, 9 or 10 C atoms.

A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1-6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Furthermore, A denotes cycloalkyl, preferably cyclopropyl, cyclobutyl, cyclopentyl, cyclohexyl, cycloheptyl, cyclooctyl or 2,6,6-trimethylbicyclo-[3.1.1]heptyl, but likewise mono- or bicyclic terpenes, preferably p-menthane, menthol, pinane, bornane or camphor, where each known stereoisomeric form is included, or adamantyl. For camphor, this denotes both L-camphor and D-camphor.

Ar denotes an unsaturated, partially or fully saturated, mono- or polycyclic homo- or heterocyclic system with the hetero atoms O, N, S which is unsubstituted or mono- or polysubstituted by Hal, A, OA, $NA_2$, $NO_2$, $NASO_2A$, $SO_2NA_2$, $SO_2A$.

Preferred cyclic systems are unsubstituted or substituted phenyl, naphthyl or biphenyl, specifically preferably phenyl, o-, m- or p-tolyl, o-, m- or p-cyanophenyl, o-, m- or p-methoxyphenyl, o-, m- or p-fluorophenyl, o-, m- or p-bromophenyl, o-, m- or p-chlorophenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-fluoro-4-bromophenyl, 2,5-difluoro-4-bromophenyl.

Particularly preferred starting materials for the aldehyde synthesis according to the invention are 5-(4-fluorophenyl) nicotinic acid morpholinamide and 5-bromonicotinic acid morpholinamide.

The present invention accordingly also relates to the use of nicotinic acid morpholinamides, preferably 5-(4-fluorophenyl)nicotinic acid morpholinamide or 5-bromonicotinic acid morpholinamide, for the preparation of the corresponding nicotinaldehydes.

The present invention furthermore relates to 5-(4-fluorophenyl)nicotinic acid morpholinamide and 5-bromonicotinic acid morpholinamide as starting materials in the synthesis according to the invention.

The reaction according to the invention is generally carried out in an inert solvent. Examples of suitable inert solvents for the reactions described above are hydrocarbons, such as hexane, petroleum ether, benzene, toluene or xylene; ethers, such as diethyl ether, diisopropyl ether, tetrahydrofuran (THF) or dioxane; glycol ethers, such as ethylene glycol dimethyl ether (diglyme); or mixtures of the said solvents. Particular preference is given to ethers, in particular tetrahydrofuran.

The amount of solvent is not crucial, in general 5 g to 500 g, preferably 10 g to 100 g of solvent can be added per g of starting material.

The reaction temperature for the reactions described above is, depending on the conditions used, between about −10° and 200°, normally between −10° and 100°, in particular between 0° and 50°, but preferably 10° to 40°, particularly preferably room temperature.

The reaction time is, depending on the conditions used, between a few seconds and several hours, preferably between 1 minute and 3 hours. However, the reaction according to the invention will very generally be complete after 0.1 to 1.5 hours.

For the purposes of this invention, the "conditions used" is taken to mean the substitution pattern of the nicotinic acid morpholinamide, the type and amount of the solvent, the type and amount of the reducing agent, the reaction duration, the reaction temperature and further details of the performance of the reaction, such as, for example, the stirrer speed or the other nature of the reaction vessel.

In general, the end of the reduction according to the invention to the aldehyde is determined by suitable analytical methods, for example thin-layer chromatography or HPLC, and the reduction is terminated.

The nicotinaldehydes according to the invention can be obtained after removal of the solvent by conventional work-up steps, such as, for example, addition of water or acid to the reaction mixture and extraction. It may be advantageous subsequently to carry out a distillation or crystallisation for further purification of the product.

The nicotinic acid morpholinamides used as starting materials for the process according to the invention can be prepared by methods known per se, as described in the literature (for example in standard works, such as Houben-Weyl, Methoden der organischen Chemie [Methods of Organic Chemistry], Georg-Thieme-Verlag, Stuttgart), to be precise under reaction conditions which are known and suitable for the said reactions. However, use can also be made of variants known per se which are not mentioned here in greater detail.

In general, the following procedure is followed:

The nicotinic acid is converted, using a suitable reagent, such as, for example, thionyl chloride, into the acid chloride, which is subsequently reacted with the desired amine to give the amide.

In order to protect substituents against undesired reactions during the reduction according to the invention and/or subsequent work-up steps, protecting groups are employed where appropriate and removed again after reduction of the nicotinic acid morpholinamide. Methods for the use of protecting groups are described, for example, in Theodora W. Green, Peter G. M. Wuts: Protective Groups in Organic Synthesis, 3rd Edition John Wiley & Sons (1999).

Even without further embodiments, it is assumed that a person skilled in the art will be able to utilise the above description in the broadest scope. The preferred embodiments should therefore merely be regarded as descriptive disclosure which is absolutely not limiting in any way.

EXAMPLE 1

Preparation of 5-(4-fluorophenyl)nicotinaldehyde from 5-(4-fluorophenyl)pyridine-3-carboxylic acid morpholinamide (a) Synthesis of the precursor 5-(4-fluorophenyl)pyridine-3-carboxylic acid Firstly, 5-(4-fluorophenyl)pyridine-3-carboxylic acid is prepared by Suzuki coupling (N. Miyaura, A. Suzuki, Chem. Rev. 95, 2457 (1995)) by reacting 5-bromonicotinic acid with p-fluorobenzeneboronic acid (both commercially available) under reaction conditions known per se to give 5-(4-fluorophenyl)pyridine-3-carboxylic acid.

(b1) Synthesis of 5-(4-fluorophenyl)pyridine-3-carboxylic acid morpholinamide—Variant 1

25.6 g of 5-(4-fluorophenyl)nicotinic acid are initially introduced in 200 ml of toluene, and 25.1 g of thionyl chloride are then added at room temperature. The mixture is then warmed at 90° C. for 18 hours, and the unreacted thionyl chloride and some of the solvent are subsequently distilled off. After the distilled-off volume has been made up with toluene, 12.4 g of morpholine are added at 80 to 100° C., and the reaction mixture is cooled after 2 hours. pH 8 is set by addition of sodium hydroxide solution, and the product is separated off by extraction with toluene. After decolourisation using activated carbon and removal of the solvent by distillation, 27.7 g of 5-(4-fluorophenyl)pyridine-3-carboxylic acid morpholinamide remain as solid (melting point: 100-102° C., yield: 81% of theory)

(b2) Synthesis of 5-(4-fluorophenyl)pyridine-3-carboxylic acid morpholinamide—Variant 2

1.2 g of Pd[P(Ph)$_3$]$_4$ and 7.6 g of p-fluorobenzeneboronic acid are added to a solution of 14.3 g of 5-bromonicotinic acid morpholinamide in 100 g of THF. A solution of 8.0 g of Na$_2$CO$_3$ in 25 g of water is subsequently added dropwise with stirring at 65° C. After 16 hours, the reaction mixture is cooled and evaporated in a rotary evaporator. The residue is taken up in dichloromethane, activated carbon is added, and the mixture is filtered. Repeated extraction of the filtrate with water and evaporation in a rotary evaporator gives a residue of 15.7 g, which, according to HPLC, comprises 89% of 5-(4-fluorophenyl)pyridine-3-carboxylic acid morpholinamide (net yield 93% of theory). Recrystallisation from ethyl acetate gives 8.0 g of 5-(4-fluorophenyl)pyridine-3-carboxylic acid morpholinamide having an HPLC purity of 99.6% (53.3% of theory).

(c) Preparation of 5-(4-fluorophenyl)nicotinaldehyde 6.0 g of 5-(4-fluorophenyl)pyridine-3-carboxylic acid morpholinamide from Example 1(b) are dissolved in 30 ml of THF, and 57 g of a 13.6% LiAlH—(OEt)$_3$ solution in THF are added over the course of 10 minutes at 30° C. to 35° C. After 1 hour, 30 ml of 12.5% sulfuric acid are added, and the organic phase is separated off. The aqueous phase is adjusted to pH 1 using sulfuric acid and extracted a number of times with methyl tert-butyl ether. The organic phases are then combined, extracted once with water and then evaporated, leaving a residue of 4.3 g having a content of 97% by weight of 5-(4-fluorophenyl)pyridine-3-carbaldehyde (yield=98% of theory).

EXAMPLE 2

Comparative Example to Example 1, Use of the piperidinamide Instead of the morpholinamide Preparation of 5-(4-fluorophenyl)nicotinaldehyde from 5-(4-fluorophenyl)pyridine-3-carboxylic acid Piperidinamide 36.7 g of 10% LiAlH$_4$ solution are diluted with 75 g of THF, and a mixture of 8.88 g of ethyl acetate and 75 g of THF is then added at 0° C. At −7° C., a solution of 6.8 g of 5-(4-fluorophenyl)pyridine-3-carboxylic acid piperidinamide in 24.7 ml of THF is added. After three hours, the mixture is added to 190 g of 10% sulfuric acid. The pH is adjusted to 3 using sodium hydroxide solution, and the THF is then substantially removed by distillation. Extraction with methyl tert-butyl ether and evaporation leaves 2.6 g of solid (content according to HPLC 67 area-%, corresp. to 36% of theory)

EXAMPLE 3

Preparation of 5-bromonicotinaldehyde from 5-bromopyridine-3-carboxylic acid morpholinamide (a) Synthesis of 5-bromopyridine-3-carboxylic acid morpholinamide 50.4 g of 5-bromonicotinic acid and 87.5 g of morpholine are heated to reflux in 200 ml of xylene, and the water formed is distilled off. After cooling, the reaction mixture is extracted three times with 10% sodium hydroxide solution and then twice with water. After the xylene has been distilled off, the residue is recrystallised from ethyl acetate. The yield after drying is 19.2 g (28.3% of theory). Melting point 80° C.

(b) Preparation of 5-bromonicotinaldehyde 1.75 g of lithium aluminium hydride powder are suspended in 64 g of THF. A mixture of 5.9 g of ethyl acetate and 28 g of THF is subsequently added dropwise with cooling. After 30 minutes, this reaction mixture is added dropwise at 0° C. to 10° C. to a solution of 5.0 g of 5-bromopyridine-3-carboxylic acid morpholinamide from Example 3(a) in 30 g of THF (this corresponds to 150% excess of the reducing agent). After 1 hour, the reaction mixture is poured into 35 ml of 12% sulfuric acid, and the organic phase is evaporated to dryness. Recrystallisation from MTB ether and drying gives 1.91 g of product (=55.7% of theory). Melting point 95° C.

As can be seen from comparison of the respective reaction yields of Examples 1 and 2, the use of the nicotinic acid piperidinamide, an alternative nicotinamide—but one which is closely structurally related to the morpholinamide—results in a significantly worse reaction.

By contrast, a better yield can be achieved on use of the morpholinamide, even with a large excess of the reducing agent (Example 3) than in the case of correct stoichiometry in Example 2, in which piperidine is used as amine component.

The invention claimed is:

1. A process for reductive preparation of a nicotinicaldehyde, said process comprising performing reduction on the corresponding nicotinic acid morpholinamide in the presence of a reducing agent to obtain said nicotinicaldehyde.

2. A process according to claim 1, wherein said nicotinic acid morpholinamide is of formula I

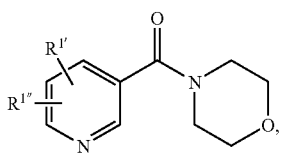

I wherein
$R^{1'}$, $R^{1'''}$ are each, independently of one another, H, Hal, A, OA, $CH_2R^2$ or Ar, $R^2$ is OA or $NA_2$, A is unbranched or branched alkyl having 1-10 C atoms, in which one or two $CH_2$ groups are each optionally replaced by an O or S atom or by a —CH=CH— group and/or also 1-7 H atoms are each optionally replaced by F, or A is cyclopropyl, cyclobutyl, cyclopentyl, cyclohexyl, cycloheptyl, cyclooctyl, 2,6,6-trimethylbicyclo[3.1.1]heptyl, p-menthane, menthol, pinane, bornane, camphor, or adamantly, Ar is an unsaturated, partially or fully saturated, mono- or polycyclic homo- or heterocyclic system wherein the hetero atoms are each O, N, or S, and which is unsubstituted or mono- or polysubstituted by Hal, A, OA, $NA_2$, $NO_2$, $NASO_2A$, $SO_2NA$, $SO_2A$, and Hal is F, Cl, Br or I.

3. A process according to claim 1, wherein said nicotinic acid morpholinamide is 5-(4-fluorophenyl)nicotinic acid morpholinamide.

4. A process according to claim 1, wherein said nicotinic acid morpholinamide is 5-bromopyridine-3-carboxylic acid morpholinamide.

5. A process according to claim 1, wherein said reducing agent is $LiAlH(OEt)_3$, $LiAlH_2(OEt)_2$ or $LiAlH_3(OEt)$.

6. A process according to claim 1, wherein said nicotinic acid morpholinamide is 5-(4-fluorophenyl)nicotinic acid morpholinamide or 5-bromonicotinic acid morpholinamide.

7. A process according to claim 1, wherein the reducing agent for said reduction is $LiAlH_{(4-n)}(OR)_n$, where n is 1, 2 or 3, and R in each case is methyl, ethyl or tert-butyl.

8. A process according to claim 2, wherein $R^{1'}$, $R^{1'''}$ are each, independently of one another, hydrogen, methoxy, ethoxy, propoxy, butoxy, fluorine, chlorine, bromine, iodine, phenyl, or o, m or p-substituted phenyl.

9. A process according to claim 2, wherein $R^{1'}$ is p-fluorophenyl or bromine and $R^{1'''}$ is hydrogen.

10. A process according to claim 2, wherein Hal is fluorine, chlorine or bromine.

11. A process according to claim 2, wherein A is unbranched or branched alkyl having 1-10 C atoms, in which one or two $CH_2$ groups are each optionally replaced by an O or S atom or by a —CH=CH— group and/or also 1-7 H atoms are each optionally replaced by F.

12. A process according to claim 11, wherein A is methyl, ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, or trifluoromethyl.

13. A process according to claim 11, wherein A is methyl, ethyl, propyl, isopropyl, butyl, isobutyl, sec-butyl, tert-butyl, pentyl, hexyl, trifluoromethyl, pentafluoroethyl, or 1,1,1-trifluoroethyl.

14. A process according to claim 2, wherein Ar is unsubstituted or substituted phenyl, naphthyl or biphenyl.

15. A process according to claim 2, wherein Ar is phenyl, o-, m- or p-tolyl, o-, m- or p-cyanophenyl, o-, m- or p-methoxyphenyl, o-, m- or p-fluorophenyl, o-, m- or p-bromophenyl, o-, m- or p- chlorophenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-fluoro-4-bromophenyl, or 2,5-difluoro-4-bromophenyl.

16. A process according to claim 2, wherein
$R^{1'}$, $R^{1'''}$ are each, independently of one another, hydrogen, methoxy, ethoxy, propoxy, butoxy, fluorine, chlorine, bromine, iodine, phenyl, or o, m or p-substituted phenyl;
Hal is fluorine, chlorine or bromine;

A is methyl, ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, trifluoromethyl, cyclopropyl, cyclobutyl, cyclopentyl, cyclohexyl, cycloheptyl, cyclooctyl, 2,6,6-trimethylbicyclo[3.1.1]heptyl, p-menthane, menthol, pinane, bornane, camphor, or adamantly; and Ar is phenyl, o-, m- or p-tolyl, o-, m- or p-cyanophenyl, o-, m- or p-methoxyphenyl, o-, m- or p-fluorophenyl, o-, m- or p-bromophenyl, o-, m- or p- chlorophenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-fluoro-4-bromophenyl, or 2,5-difluoro-4-bromophenyl.

17. A process according to claim 2, wherein the reduction is carried out in an inert solvent, and said solvent is selected from hexane, petroleum ether, benzene, toluene or xylene; ethers, such as diethyl ether, diisopropyl ether, tetrahydrofuran, dioxane, ethylene glycol dimethyl ether, and mixtures of thereof.

18. A process according to claim 17, wherein the amount of solvent is 10 g to 100 g of solvent per g of nicotinic acid morpholinamide.

19. A process according to claim 2, wherein the reduction is performed at a temperature between −10° and 100°.

20. A process according to claim 17, wherein the reduction is performed at a temperature between −10° and 100°.

* * * * *